United States Patent [19]

Guttman

[11] Patent Number: 5,503,722
[45] Date of Patent: Apr. 2, 1996

[54] REHYDRATABLE GELS FOR CAPILLARY ELECTROPHORESIS

[75] Inventor: Andras Guttman, Irvine, Calif.

[73] Assignee: Beckman Instruments, Inc., Fullerton, Calif.

[21] Appl. No.: 203,168

[22] Filed: Feb. 28, 1994

[51] Int. Cl.$^6$ ............................. B01D 57/02; C25B 7/00
[52] U.S. Cl. ........................... 204/450; 204/455; 204/470
[58] Field of Search ........................ 204/182.8, 180.1, 204/299 R; 526/303.1

[56] References Cited

U.S. PATENT DOCUMENTS

| | | | |
|---|---|---|---|
| 3,578,604 | 5/1971 | Uriel | 252/316 |
| 3,875,044 | 4/1975 | Renn et al. | 204/299 |
| 3,878,100 | 4/1975 | Bixler | 210/198 |
| 3,957,739 | 5/1976 | Cabestany et al. | 526/303.1 |
| 4,006,069 | 2/1977 | Hiratsuka et al. | 204/180 |
| 4,048,377 | 9/1977 | Boschetti et al. | 428/474 |
| 4,189,370 | 2/1980 | Boschetti | 204/299 |
| 4,737,533 | 4/1988 | Charmot et al. | 524/22 |
| 4,746,551 | 5/1988 | Allen et al. | 427/389.7 |
| 4,948,480 | 8/1990 | Christy, Jr. et al. | 204/182.8 |
| 4,999,340 | 3/1991 | Hoffman et al. | 514/23 |
| 5,264,101 | 11/1993 | Demorest et al. | 204/299 R |

FOREIGN PATENT DOCUMENTS

0340653A2  8/1989  European Pat. Off. ....... G01N 27/26

*Primary Examiner*—John Niebling
*Assistant Examiner*—Edna Wong
*Attorney, Agent, or Firm*—William H. May; Janis C. Henry

[57] ABSTRACT

Compositions useful as a separation medium in capillary electrophoresis procedure and methods for their use in capillary electrophoresis are described. The compositions include dry linear polyacrylamide which is capable of hydrating to form an aqueous polymeric system capable of filling an electrophoresis capillary column. Also disclosed are methods for using dry polyacrylamide in capillary electrophoresis. The methods include providing a dry polyacrylamide composition, reconstituting the dry polymer to provide a solution of reconstituted polymer, and causing the reconstituted polymer to fill a capillary electrophoresis column.

12 Claims, 1 Drawing Sheet

REHYDRATABLE GELS FOR CAPILLARY ELECTROPHORESIS

BACKGROUND OF THE INVENTION

1. Field of the Invention

The present invention relates generally to separation mediums utilized in capillary electrophoresis procedures. More particularly, the present invention involves hydratable polyacrylamide compositions and methods for using polyacrylamide compositions in capillary electrophoresis applications. The present invention provides separation mediums having indefinite shelf life and which provide reproducible high resolution electrophoretic separations.

2. Description of Related Art

Electrophoretic separation techniques have been utilized for years to separate molecules according to differences in the effective charge of the molecules, and/or according to differences in the molecular size of the molecules. Up until recently electrophoretic separations were conducted in gel slabs open beds which were typically fabricated of polyacrylamide gel material. More recently, capillary electrophoresis procedures have been developed which provide high resolution separations of molecules having different effective charges and/or different masses. These procedures typically involve applying electrophoretic principles to buffer filled or gel filled narrow capillary tubes.

Typically, capillary columns used in capillary electrophoresis are fabricated of silica tubing having diameters on the order of 15 μm to 200 μm and lengths from about 10 to 200 cm. High resolution separation of charged compounds is by applying an electric field across the column which causes the compounds to electrophoretically migrate in the gel and/or buffer. Numerous types of molecules including peptides, proteins, oligonucleotides, nucleic acids and other molecular species can be rapidly and economically separated utilizing these techniques.

In the past, gel filled capillary columns have been supplied directly to researchers or other electrophoretic capillary column users. One problem associated with gel filled commercial columns relates to gel stability. Since aqueous polyacrylamide gels tend to break down or degrade at ambient temperatures, these columns and have limited useful shelf lives and usefulness. As an alternative to the direct purchase of gel filled columns, manufacturers have supplied gels in vials. Users can then remove gels from columns when they show signs of degrading and utilize pumping systems on automated electrophoresis instruments to fill capillaries by forcing gel from the vial and into the column. Advantageously, this approach allows the gel capillary user increased control over the electrophoresis separations because as soon as the gel shows a decrease in separation performance it is a simple procedure to rapidly change the gel in the column.

Another method of providing capillaries with the necessary gel for carrying out electrophoresis procedures involves the user filling the capillary with a precise amount of gel monomer, e.g. acrylamide, in an aqueous system. Then the monomer is polymerized, in situ, to form the aqueous based gel. This system has the disadvantage of being very time consuming and requires a certain amount of polymerization procedure know-how.

With the ability to pump fresh gel into capillary columns and perform in-situ polymerizations, the high costs associated with directly purchasing gel filled columns is significantly decreased. However, disadvantages relating to the instability of aqueous polyacrylamide gels and the time required to perform polymerization are still problems. In particular, when aqueous gels are stored in vials and intended for use in replaceable gel systems they are subject to degradation which is exemplified as rapid changes in gel flow characteristics and electrophoresis separation performance. What is more, the degradation of aqueous gels is an ongoing process and the degree of degradation increases with time. Thus, electrophoretic separations in gel filled columns and replaceable gel systems are seldom reproducible from one column or one gel filling to the next.

Accordingly, it is an objective of the present invention to provide compositions having improved handling properties as separation mediums in capillary electrophoresis procedures.

It is additionally an objective of the present invention to provide compositions having extended shelf lives and useful as separation mediums in capillary electrophoresis procedures.

It is further an objective of the present invention to provide methods for utilizing long shelf life separation mediums in capillary electrophoresis separations.

It is additionally an objective of the present invention to provide methods for preparing gel-filled capillary electrophoresis columns.

SUMMARY OF THE INVENTION

The present invention satisfies the above-identified objectives by providing compositions which are useful as separation mediums in capillary electrophoresis and which have substantially unlimited shelf life. The compositions of the present invention can be stored indefinitely and then rapidly treated and placed in the interior of capillaries for use in electrophoretic separations. Thus, unlike prior art capillary electrophoresis gels which, over a relatively short time period, lose their ability to provide mediums for high resolution and efficient electrophoretic, the compositions of the present invention have unlimited shelf lives.

Advantageously, the compositions of the present invention lend themselves to a number of different electrophoretic separation conditions including those separation systems requiring gel additives such as pH buffer compounds, urea, formamide and SDS. Furthermore, additives useful in affinity separations and chiral based separations are also conveniently controlled in the use of the compositions described herein. Moreover, gel based capillary electrophoresis methods requiring different buffer compounds are readily accommodated by the use of the compositions described herein.

In particular, the present invention provides compositions useful as a separation medium in capillary electrophoresis procedures. The compositions are essentially dry linear polyacrylamide which are capable of hydrating to form an aqueous polymeric gel capable of filling a capillary electrophoresis column.

In an alternative embodiment of the present invention, the dry linear polyacrylamide additionally includes additives such as buffering compounds, urea, sodium dodecyl sulfate, and additives which promote specific types of electrophoretic techniques such as chiral based separations and affinity enhanced separations.

Also disclosed herein are methods for the preparation and utilization of compositions of the present invention in capillary columns useful in capillary electrophoresis. More specifically, an exemplary method for using hydratable linear polyacrylamide in electrophoresis gel systems involves providing a composition of dry polyacrylamide and reconstituting the dry polyacrylamide in a liquid to form an electrophoresis gel. Then causing the reconstituted polymer to fill a capillary electrophoresis column provides a fresh gel filled column. Advantageously, capillaries filled with reconstituted polyacrylamide have all of the functional characteristics of fresh gel columns without the uncertainty associated with columns filled with replaceable gel which has been stored.

It is contemplated to be within the present invention to reconstitute the dry polyacrylamide with liquids which may include electrophoresis gel additives such as urea, formamide, sodium dodecyl sulfate, and additives for performing chiral and affinity electrophoresis.

These and other advantages associated with the present invention will become apparent to those skilled in the art upon an understanding of the invention as described in the detailed description of the invention in combination with the drawings described briefly as follows.

DETAILED DESCRIPTION OF THE INVENTION

Figure 1:
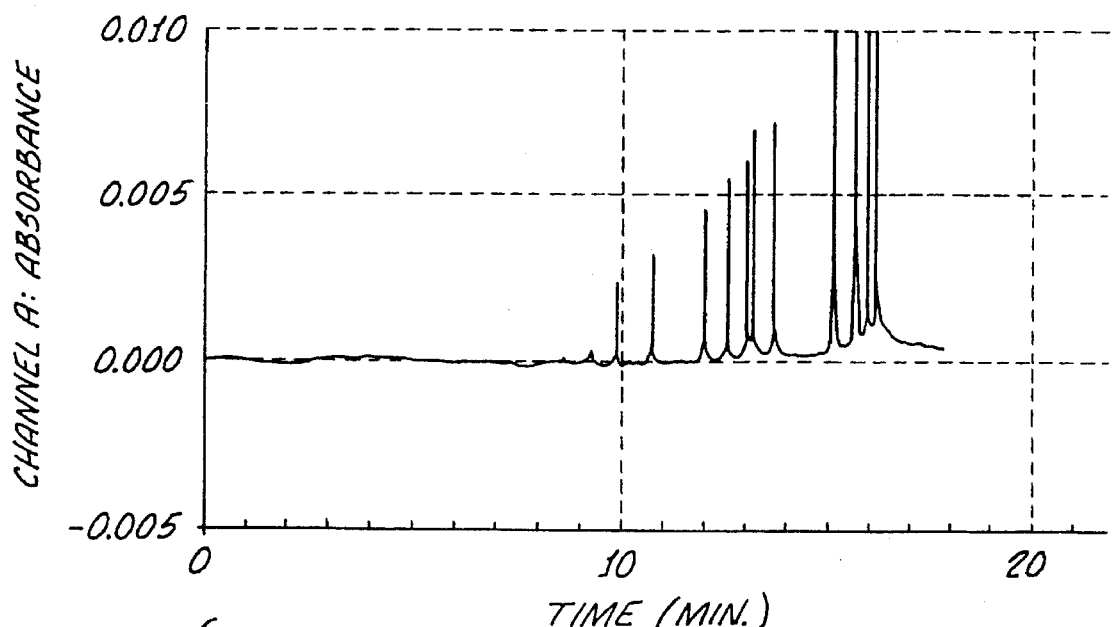
FIG. 1 is an electropherogram obtained from the electrophoretic separation of PhiX-174 DNA restriction fragments test mixture utilizing freshly polymerized linear polyacrylamide gel filled capillary column.

The present invention provides compositions and methods for utilizing the compositions in capillary electrophoresis systems. In particular the compositions and method of the present invention are useful in electrophoretic separation systems such as the P/ACE series Capillary Electrophoresis Systems manufactured and sold by Beckman Instruments, Inc., Fullerton, Calif. Preferably the capillary electrophoresis system is equipped with a means for filling electrophoresis capillaries with gel compositions.

The compositions of the present invention and methods for their use are superior to prior art compositions and methods in that they provide the capillary electrophoresis user added assurance that the separation medium will perform in a predictable and effective manner. That is, prior art gel compositions have limited shelf life because they tend to degrade and otherwise lose their effectiveness as a medium for the high resolution and reproducible separation of charged compounds. The compositions of the present invention have unlimited shelf life because they are not exposed to degrading environment common to prior art compositions. When capillary electrophoresis columns are filled with the treated compositions of the present invention to provide gel filled columns, the gel retains the high resolution separation properties of freshly prepared gel. This is because the column is filled with a polymer system which has been free of moisture during its period of non-use.

Advantageously, the compositions described herein are suitable for use in a wide variety of different capillary electrophoresis separation methodologies in which gel is the separation medium. For example, virtually any buffer can be incorporated into the compositions described herein and additives commonly used in capillary electrophoresis gels are easily utilized in the present invention. Although the compositions and columns of the present invention are generally find application for the electrophoretic separation of charged compounds, a particularly suitable application is the electrophoretic separation of DNA.

More specifically, the compositions of the present invention are useful in capillary electrophoresis procedures and essentially includes dry linear polyacrylamide which is capable of hydrating to form an aqueous polymeric gel suitable for filling a capillary electrophoresis column. As known in the art, polyacrylamide is hydrophilic and possesses a certain degree of affinity for moisture which is difficult to exclude from the polymer. However, the linear polyacrylamide of the present invention is sufficiently dry to have negligible moisture driven degradation and sufficiently dry to have a physical configuration in the form of a dry pourable powder. As described in greater detail below, the dry linear polyacrylamide compositions of the present invention are conveniently reconstituted in a liquid and used to fill capillary electrophoresis columns for subsequent use in electrophoretic separations.

Another property characteristic of polyacrylamide compositions of the present invention is the linear nature of the polymer. Unlike polyacrylamides utilized in slab gel electrophoresis systems which are prepared with cross-linking reagents to provide a cross-linked polymer having a particular physical form, the polyacrylamides used herein are preferably prepared in the absence of cross-linking reagents. This results in a linear polyacrylamide which is more easily dissolved when rehydrated or reconstituted as compared to a cross-linked polyacrylamide which swells when rehydrated or reconstituted. It is recognized that very small amounts of cross-linking agents can be utilized to polymerize acylamide monomer and obtain polymer having such a low degree of cross-linking that the polymer is apparently soluble. Thus, "linear" polymer in the context of the present invention applies to polymer which appears to freely dissolve and have flow properties which allow solutions of the polyacrylamide to fill a capillary column having diameters on the order of 15 μm–200 μm.

Once reconstituted, the polyacrylamide compositions of the present invention are freely flowing to the extent that they can be used to fill a capillary electrophoresis column. This differs from dry cross-linked polyacrylamide which retains its dry shape and form after reconstitution because it swells in the reconstitution fluid and does not dissolve.

As a feature of the present invention the dry, linear polyacrylamide can further include additives useful in capillary electrophoresis separation mediums. These additives include but are not limited to pH buffer compounds, urea, sodium dodecyl sulfate, and formamide. In exemplary embodiments of the present invention, the additives are incorporated into the dry linear polyacrylamide at concentrations which are conventionally used in capillary electrophoresis systems. Those skilled in the art will appreciate that the concentration of such additives will vary depending upon the desired final concentration of the reconstituted dry linear polyacrylamide.

For example, when the dry linear polyacrylamide is reconstituted to a final concentration of 6 wt % in water and urea is desired in the final reconstituted composition at a level of 8 molar, for every 6 grams of dry linear polyacrylamide composition there is incorporated therein 48 grams of urea. (Urea has a molecular weight of 60). Similarly, in the same 6 wt % reconstituted polyacrylamide, when sodium dodecyl sulfate (SDS) is desired at a final reconstituted concentration of 0.5 wt %, the 6 grams of the dry linear polyacrylamide composition includes 0.5 grams of SDS.

As known in the art, typical concentrations of urea in polyacrylamide separation mediums range from about 7 to 9 molar. Similarly, separation mediums which include formamide incorporate this additive at up to 70 wt % and preferably between 30 wt % to 45 wt %. When sodium dodecyl sulfate is desired in electrophoresis separation mediums, it can be present from 0.1 wt % to 1 wt %. A wide variety of pH buffering compounds have been utilized in capillary electrophoresis systems and are suitable for a number of different separation applications. These buffers include but are not limited to phosphates, borates, barbiturates, and acetates. For purposes of the present invention, the preferred pH buffer compound additives include tris borate and tris acetate at concentration which range from 50 mM to 100 mM and adjusted to a pH of 8–8.5. Other additives which may be useful in the dry linear polyacrylamide compositions of the present invention include those which promote chiral based separations or affinity based separation under capillary electrophoresis conditions. For example, ethidium bromide can be incorporated in polyacrylamide separation mediums at from about 0.1 µM–10 µM to enhance affinity separations. In order to enhance the electrophoretic separation of enantiomers, cyclodextrins can be incorporated in the separation medium at concentration of from about 2 mM to 200 mM.

The preparation of linear polyacrylamide is credited to those skilled in the art and it can be appreciated by those skilled in the art that a number of different initiators and polymerization conditions are suitable for polymerizing acrylamide to form polyacrylamide. Since acrylamide is water soluble and many initiators and catalysts useful in acrylamide polymerizations are also water soluble, water is a convenient polymerization solvent. A typical exemplary polymerization process involves dissolving acrylamide monomer in a solvent, usually water, adding initiators and catalyst such as ammonium persulfate and TEMED, respectively, and then vacuum degassing the solution to remove oxygen which inhibits the polymerization. Although room temperature polymerizations (about 25° C.) are preferred, gentle warming to 40° or 50° C. can be used to speed the polymerization. Similarly, cooling to 0° C. can be used to slow the polymerization. After the polymerization is complete, typically within 3 to 6 hours, the resulting polyacrylamide solution is subjected to conditions which separate the water from the polymer. The polyacrylamide can be precipitated from solution using a water soluble non-solvent for the polymer and then dried with gentle heating and under vacuum. It is also desirable to redissolve the polyacrylamide in water and repeat the precipitation procedure to remove excess catalyst, initiator, and monomer which may have originally precipitated with the polymer.

Finally, the polyacrylamide is thoroughly dried to provide the final dry polyacrylamide composition. The drying process can be selected according to equipment and time available. For example, applying vacuum and heat to the polyacrylamide will drive sufficient water from the composition to provide a composition with the requisite low amount of moisture content. Applying vacuum alone or applying gentle heat alone (up to 50° C.) will also provide a sufficiently dry composition. Alternatively, lyophilizing the polyacrylamide solution or precipitated polyacrylamide will give the desired dry acrylamide in powder form.

In preparing polyacrylamide in aqueous solution, the initial acrylamide concentration can be selected according to the length of time allowed for the polymerization and the desired final concentration of polyacrylamide in the reconstituted product. In particular, it is preferred that the initial monomer concentration be about the same concentration or a lower concentration than the desired final polyacrylamide concentration in the reconstituted or rehydrated separation medium. For example, if 2 wt % acrylamide is utilized in the solution, the final reconstituted polymer concentration is preferably less or equal to 2%. Additionally, as known in the art, the concentration of initiator and catalyst utilized in the polymerization should be varied according to the acrylamide concentration and generally increases with increased monomer concentration.

Once formed, the dry linear polyacrylamide compositions of the present invention advantageously have a substantially unlimited shelf life. That is, when stored at reduced temperatures of between 0°–5° C. and excluded from light, air and moisture, the compositions remain stable and do not degrade. Advantageously, and primarily because of the stability of the dry linear polyacrylamide composition, when they are used in capillary electrophoresis applications in accordance with the present invention, the compositions notably contribute to the reproducibly high resolution separation of many types of compounds.

In accordance with the present invention methods for using dry linear polyacrylamide in capillary electrophoresis involve providing a dry linear polyacrylamide composition described herein and reconstituting the dry linear polymer to provide a solution of reconstituted linear polymer. Then causing the reconstituted polymer to fill a capillary electrophoresis column provides a separation medium filled column suitable for a variety of electrophoretic separations. In exemplary embodiments of the present invention providing the dry polyacrylamide composition can be accomplished as described above. That is, a solution of acrylamide is polymerized to form polyacrylamide and the polyacrylamide is retrieved from the solution by removing the polymerization solvent from the solution. Then the polyacrylamide is further dried according to any method suitable for drying polyacrylamide while avoiding hydrolytic or heat accelerated degradation.

In order to provide a reconstituted polymer the dry polyacrylamide and a liquid are combined to form a polyacrylamide and liquid mixture. Then mixing the polyacrylamide and liquid mixture to form a homogeneous mixture provides a reconstituted polyacrylamide suitable as a separation medium in electrophoresis procedures. In preferred embodiments the liquid is water and the reconstitution step is a rehydration. However, it is contemplated to be within the scope of the present invention to utilize alternative liquids such as ethylene glycol as reconstitution liquids.

The concentration of polyacrylamide in the final rehydrated form can vary from as little as 0.01 wt % to 10 wt %. However, the preferred concentration is in the range of 3–6 wt %. The general principles known in the art relating to the concentration of separating medium utilized in electrophoresis procedures apply in the practice of the present invention. For example, for applications involving the separation of DNA fragments, typically the greater the number of base pairs found in the DNA fragments being separated, the greater the concentration of linear polyacrylamide. For DNA fragments having base pairs in the range of up to 23,000, concentrations of about 3 wt % are preferred. For DNA fragments having lower numbers of base pairs, such as less than 3,000, higher concentrations of linear polyacrylamide are preferred.

Thus, in selecting the amount of dry polyacrylamide to rehydrate, one should first consider the desired electrophoretic application. It is also desirable to consider the concentration of acrylamide in the polymerization solution utilized to prepare the dry polyacrylamide. Since in preferable embodiments the final concentration of polyacrylamide in the rehydrated mixture should be about the same or less than the concentration utilized in the original polymerization solution, a dry linear polyacrylamide prepared in a solution of the appropriate concentration of acrylamide is preferably selected.

Another consideration in preparing rehydrated polyacrylamide solutions is the nature of any pH buffer compounds and other additives useful in selected electrophoresis procedures. As mentioned above, exemplary embodiments of the present invention can incorporate pH buffer compounds and other additives useful in electrophoresis separation mediums in the dry polyacrylamide composition. In such cases the water utilized in the rehydration is typically double distilled water and contains no further additives.

However, it is fully within scope of the present invention to incorporate electrophoresis pH buffering compounds in the rehydration water as an alternative to incorporating the pH buffering compounds in the dry linear polymer composition. In cases where pH buffer compounds and additives are intended to be incorporated in the rehydrating solution, the rehydrating solution should be prepared to contain the desired additives with consideration of their desired final concentration. Suitable buffering compounds and exemplary buffering compound concentrations in the final separation medium are described above and will not be repeated here.

With respect to suitable electrophoresis separation medium additives for incorporating in the rehydrating water these include but are not limited to urea, formamide, sodium dodecyl sulfate, ethidium bromide, and cyclodextrins. As mentioned above, these additives have known properties useful in providing stable electrophoresis separating mediums and in providing certain performance characteristics to the separation mediums.

In cases where the rehydration water includes the pH buffering compounds or other additives useful in the contemplated electrophoresis procedures, the same principles described above relating to concentration of these additives and compounds in the water apply. For example, when an 8 molar final concentration of urea is desired, every 100 mL of rehydrating water contains 48 grams of urea. Similarly, when sodium dodecyl sulfate (SDS) is a preferred additive at 0.5 wt %, each 100 mL of rehydrating water contains 0.5 grams of SDS.

To rehydrate dry linear polyacrylamide in accordance with the present invention, the appropriate amount of linear polyacrylamide and rehydration water containing additives, if desired, are combined in a vessel equipped with a mixer. The resulting mixture is stirred continuously for 1–3 hours until an homogeneous system is obtained. The homogeneous mixture is suitable for use as a separation medium in capillary electrophoresis and can be easily incorporated in a capillary electrophoresis column.

Although any column useful in capillary electrophoresis procedures is suitable for use in combination with the rehydrated compositions of the present invention, preferred columns are silica capillary columns having dimensions which range from a diameter of about 15 µm to about 200 µm and a length of from about 1-cm to about 200 cm. As known in the art, the surface of silica capillary columns has SiOH functionalities. When exposed to the electric field generated during electrophoresis separations, the SiOH functionalities ionize to provide a negatively charged $SiO^-$ surface. The protons near the surface of the silica migrate under the influence of the electric field. This effect results in an electroosmotic bulk flow of liquid within the capillary column. Such electroosmotic flow can be used beneficially or it can be reduced or eliminated in certain applications as desired. For example, to substantially reduce electroosmotic flow in capillary electrophoresis, capillary columns can be coated on their interior surface with a polymeric coating. This reduces the degree of SiOH ionization, thus substantially reducing the amount of electroosmotic flow.

In preferred embodiments of the present invention, the rehydrated dry polyacrylamide is utilized to fill capillary electrophoresis columns which have been treated in a manner designed to reduce or eliminate electroosmotic flow. An exemplary embodiment involves capillary columns having coated interior wall surfaces. Preferably, the coated interior wall surface has a hydrophilic polymer coating such as a coating of film forming polyacrylamide.

In accordance with the present invention causing the reconstituted polyacrylamide to fill a capillary electrophoresis column typically involves simply forcing the reconstituted or rehydrated polyacrylamide into the selected capillary. Those skilled in the art are credited with the knowledge required for these processes. In particular, it is convenient to take advantage of pumping systems provided on automated capillary electrophoresis instrumentation. These pumping systems are useful for filling columns with commercially available prepared gels and for pumping spent gels from the columns. Other uses for the pumping systems involve pumping in monomer solutions for the in situ polymerization of monomer to form the desired gel separation medium. In using the available pumping systems, the rehydrated linear polyacrylamide compositions described herein are used in the same capacity as the commercially available gel compositions. The conditions used for pumping the rehydrated linear polyacrylamide are essentially the same as used for filling capillaries in general.

Subsequent to filling the capillary with the rehydrated linear polyacrylamide mixtures, the filled columns are suitable for the electrophoretic separation of a variety of compounds, including but not limited to DNA fragments, proteins, peptides, and other compounds such as basic drugs. Advantageously, the rehydratable dry polyacrylamide compositions can be stored indefinitely and shipped without costly climate control considerations. Because they are dry compositions, problems associated with degradation and hydrolysis of prior art gels are overcome. Finally, users of the dry linear polyacrylamide compositions described herein are assured that rehydrated linear polyacrylamide used in capillary electrophoresis columns will reproducibly support high resolution electrophoretic separations.

Having now generally described the invention, the same will be more readily understood through reference to the following examples which are provided by way of illustration, and are not intended to be limiting of the present invention, unless specified.

EXAMPLE 1

The following illustrates a process for preparing polyacrylamide for subsequent dehydration to form the compositions of the present invention. This example also illustrates the electrophoretic separation characteristics of polymerized acrylamide as a separation medium for DNA restriction fragments.

Twelve grams of acrylamide were combined with 100 mLs of double distilled water, ammonium persulfate and TEMED. The resulting 12 w/v % acrylamide solution was degassed under vacuum and the polymerization was allowed to proceed for 3 hours at room temperature. After the polymerization was complete, the solution was diluted to a total polymer concentration of 3% and sufficient tris borate was added to the solution provide a tris borate concentration of 100 mM.

A silica capillary electrophoresis column having an interior surface coating of polyacrylamide, an overall length of 27 cm and a diameter of 100 μM was install on a P/ACE capillary electrophoresis system and sufficient 3% polyacrylamide, tris borate solution was pumped into the column. A mixture of PhiX-174 DNA restriction fragments was separated in the capillary using a voltage of 300 V/cm and uv detection at 254 nm. The results of the separation are shown in FIG. 1. This figure indicates baseline separation of the fragments within 17 minutes under the stated conditions.

EXAMPLE 2

The following example illustrates an exemplary procedure for dehydrating, rehydrating and utilizing polyacrylamide compositions in accordance with the present invention.

Acrylamide monomer was polymerized according to the polymerization procedure described in EXAMPLE 1. Then water was removed from the solution by subjecting the solution to slight warming (40° C.) under a 100 mbar vacuum. The resulting dry polyacrylamide was a powder consistency and was capable of freely flowing. Then, three grams of the dry polyacrylamide was added to 100 mLs of aqueous 100 mM tris borate. The mixture was stirred continuously for 1.5 hours under a homogeneous system of rehydrated polyacrylamide was formed.

Figure 2:
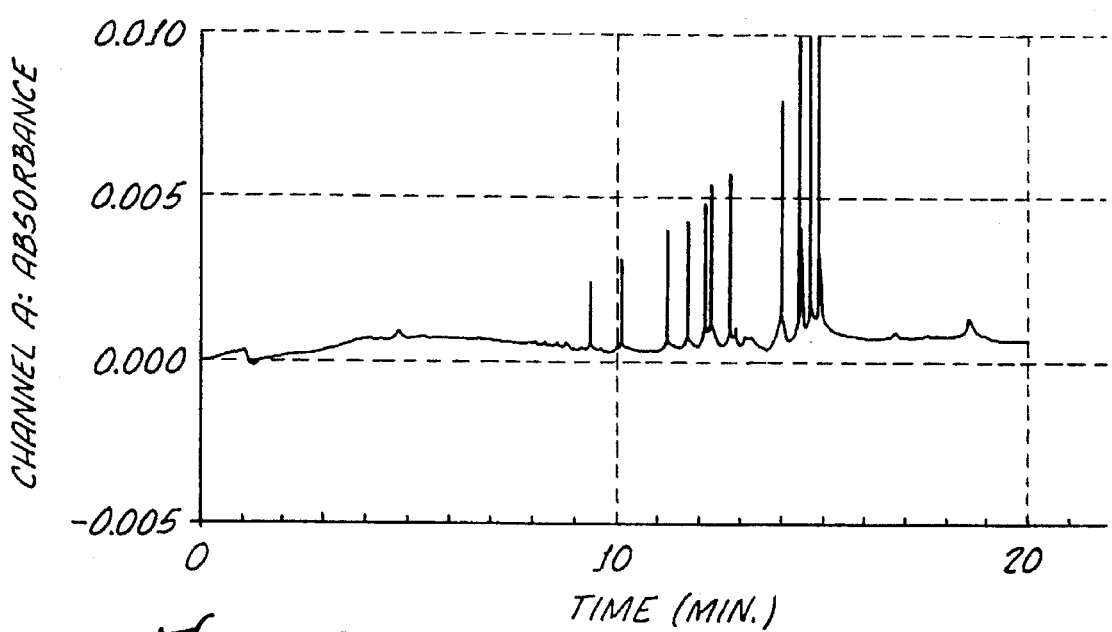
FIG. 2 is an electropherogram obtained from the electrophoretic separation of Phix-174 DNA restriction fragments test mixture using the same conditions as those used to obtain the electropherogram of FIG. 1 except that the linear polyacrylamide was dried, then rehydrated and pumped into the capillary column.

A silica capillary electrophoresis column having an interior surface coating of polyacrylamide, an overall length of 27 cm and a diameter of 100 μM was install on a P/ACE capillary electrophoresis system and sufficient 3% polyacrylamide, tris borate solution was pumped into the column. A mixture of PhiX-174 DNA restriction fragments was separated in the capillary using a voltage of 300 V/cm and uv detection at 254 nm. The results of the separation are shown in FIG. 2. This figure indicates baseline separation of the fragments within 17 minutes under the stated conditions. Upon comparing the electropherograms of FIG. 1 and FIG. 2 it is clear that the two separations are substantially identical. Thus, using dehydrated and rehydrated polyacrylamide in accordance with the present invention provides all the separation performance of fresh gel and at the same time provides the added advantages of indefinite gel shelf life and user versatility.

What is claimed is:

1. A process for using dry linear polyacrylamide in capillary electrophoresis, said process comprising the steps: providing a dry linear polyacrylamide composition;

reconstituting said dry linear polyacrylamide to provide a solution of reconstituted linear polyacrylamide; and causing said reconstituted linear polyacrylamide to fill a capillary electrophoresis column.

2. The process of claim 1 wherein providing said dry linear polyacrylamide composition includes the steps of:

causing a liquid solution of acrylamide monomer to polymerize under conditions suitable for forming a liquid solution of linear polyacrylamide;

removing said liquid from said liquid solution of linear polyacrylamide to provide a dry linear polyacrylamide.

3. The process of claim 2 wherein causing a liquid solution of acrylamide monomer to polymerize is accomplished by forming an aqueous solution of acrylamide and polymerization initiator, removing oxygen from said aqueous solution wherein said acrylamide monomer forms linear polyacrylamide.

4. The process of claim 2 wherein removing said liquid from said liquid solution of polyacrylamide is accomplished by applying a vacuum to a container of said liquid solution.

5. The process of claim 4 further including warming said liquid solution.

6. The process of claim 1 wherein reconstituting said dry linear polyacrylamide comprises combining dry linear polyacrylamide and water to form a polyacrylamide and water mixture.

7. The process of claim 6 further including the step of mixing said polyacrylamide and water mixture until a homogeneous composition is obtained.

8. The process of claim 6 wherein said water further includes electrophoresis pH buffering compounds.

9. The process of claim 6 wherein said water further includes electrophoresis separation medium additives selected from the group consisting of urea, formamide, sodium dodecyl sulfate, ethidium bromide, and cyclodextrins.

10. The process of claim 1 wherein said dry linear polyacrylamide composition further includes pH buffering compounds.

11. The process of claim 1 wherein said dry linear polyacrylamide composition further includes electrophoresis separation medium additives selected from the group consisting of urea, formamide, sodium dodecyl sulfate, ethidium bromide, and cyclodextrins.

12. The process of claim 1 wherein causing said solution of reconstituted linear polyacrylamide to fill a capillary electrophoresis column comprises the step of pumping said solution of reconstituted linear polyacrylamide into a capillary electrophoresis column.

* * * * *